United States Patent [19]
Biber

[11] Patent Number: 5,898,518
[45] Date of Patent: Apr. 27, 1999

[54] STEREO MICROSCOPE ARRANGEMENT

[75] Inventor: Klaus Biber, Aalen, Germany

[73] Assignee: Carl-Zeiss-Stiftung, Germany

[21] Appl. No.: 08/555,453

[22] Filed: Nov. 13, 1995

[30]    Foreign Application Priority Data

Nov. 19, 1994  [DE]    Germany .......................... 44 41 277.0

[51] Int. Cl.⁶ .......................... G02B 21/06; G02B 21/26
[52] U.S. Cl. .......................... 359/385; 359/387; 359/388; 359/375; 359/390; 359/392
[58] Field of Search ..................... 359/385, 387, 359/388, 372, 373, 374, 376, 375, 390, 392, 389

[56]               References Cited

U.S. PATENT DOCUMENTS

| 2,103,230 | 12/1937 | Benford et al. | 359/389 |
| 3,776,614 | 12/1973 | Kloots et al. | 359/376 |
| 4,991,947 | 2/1991 | Sander et al. | 359/375 |
| 5,052,789 | 10/1991 | Kleinberg | 359/375 |
| 5,126,877 | 6/1992 | Biber | 359/389 |

FOREIGN PATENT DOCUMENTS

| 0 363 762 | 4/1990 | European Pat. Off. | |
| 1113314 | 8/1961 | Germany | 359/390 |
| 251414 | 11/1987 | Germany | 359/385 |
| 4105221 | 9/1991 | Germany | 359/385 |
| 40 28 605 | 3/1992 | Germany | |
| 93 14 578 | 11/1993 | Germany | |
| 43 31 635 | 6/1994 | Germany | |
| 406250091 | 9/1994 | Japan | 359/376 |
| 94002872 | 2/1994 | WIPO | 359/385 |

OTHER PUBLICATIONS

U.S. application No. 08/223,333, Sander, filed Apr. 5, 1994.

*Primary Examiner*—Cassandra Spyrou
*Assistant Examiner*—Mohammad Y. Sikder

[57]            ABSTRACT

A stereo microscope arrangement includes an objective used in common, at least a first and a second pair of stereoscopic observation beam paths and an illuminating unit with at least one deflecting element that deflects illuminating light in the direction of the object plane. The illuminating unit is arranged so that it can be mounted in at least two different positions relative to the stereoscopic beam paths. Accordingly, optimized illuminating conditions can be selectively placed at the disposal of the main observer or the co-observer.

12 Claims, 2 Drawing Sheets

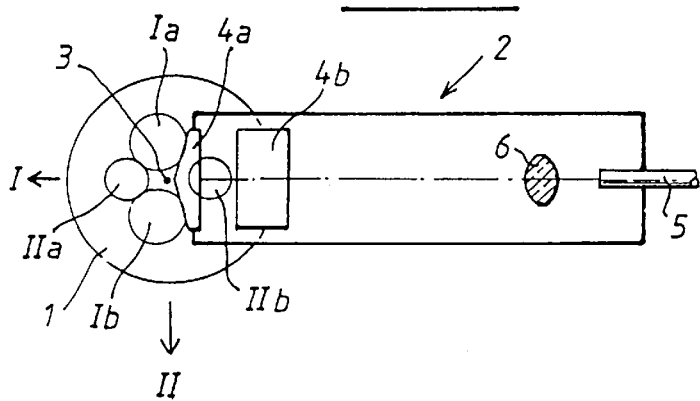
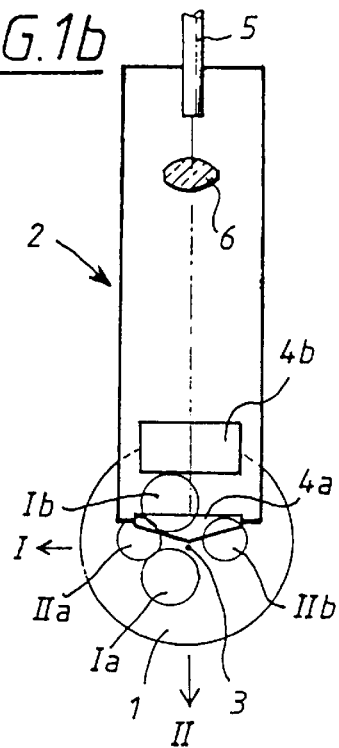
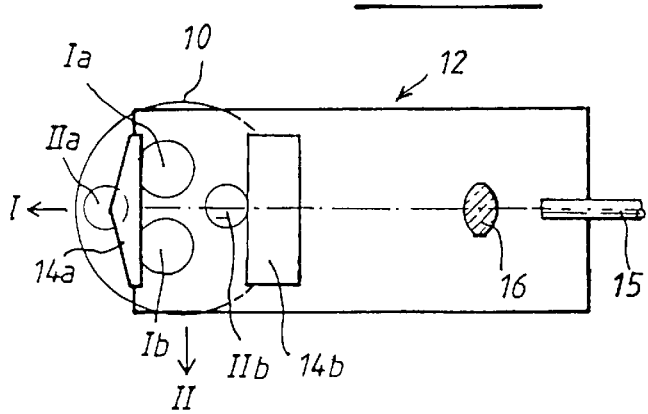
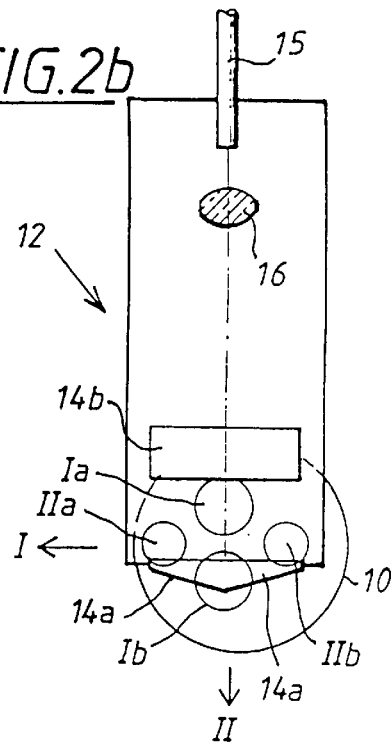

STEREO MICROSCOPE ARRANGEMENT

BACK GROUND OF THE INVENTION

1. Field of the Invention

The present invention relates to a stereo microscope arrangement with an objective that is used in common and that has at least two pairs of stereoscopic observation beam paths passing through it. The present invention also relates to a suitable illumination unit for such an arrangement.

2. Discussion of Prior Art

Stereo microscopes for use in microsurgery are known which, besides a main observer tube with a first pair of stereoscopic observation beam paths, furthermore have a so-called co-observer tube with a second pair of stereoscopic observation beam paths, that is, a co-observer microscope that is optically and mechanically coupled to the main observer microscope. As regards illumination, such arrangements usually include an illumination unit that is dimensioned to be optimum for only one of the two observers, or only one observation beam path pair. The illumination is preferably optimized for the stereoscopic beam path pair of the main observer, or for the main observer microscope.

An optimum configuration of illumination is important, and particularly so in the field of ophthalmic surgery, when in cataract operations as good as possible a "red reflection" is required, which serves to make the remainder of the lens visible with high contrast. For a stereo microscope without a co-observer microscope, an illuminating device is known to be advantageous which is described in U.S. Pat. No. 5,126,877, which issued Jun. 30, 1992. Two deflecting elements are provided there in the illuminating beam path, and deflect light into the object plane at different angles relative to the optical axis of the main objective.

SUMMARY OF THE INVENTION

The object of the present invention is to make at least optionally available to a co-observer, in such a stereo microscope arrangement, the advantages of an illuminating device which is optimized for the main observer, as is known, for example, from U.S. Pat. No. 5,126,877. However, even with a non-optimum illuminating configuration, at least a satisfactory illumination is to be provided for the co-observer or for the main observer.

These objects are achieved according to the present invention by a stereo microscope arrangement having an illuminating unit that can be mounted in at least two different positions relative to the optical axis of the objective that is used in common.

It is now ensured, due to the arrangement or embodiment, according to the invention, of the illuminating unit, that selectively either the main observer or the co-observer has the optimized illuminating configuration at his disposal. This takes place by a simple mounting, or else rotation, of the illuminating unit in the desired position. Thus the main operator, perhaps during an operation, can temporarily also place the illuminating unit, which is optimized for him, at the disposal of an assistant. According to the position of the illuminating unit relative to the stereoscopic observation beam paths, the assistant then receives the optimized image impression presented for the main observer, and vice versa. Neither the main observer nor the co-observer has to change his working position, which is particularly important during an operation.

Moreover it is ensured by the corresponding dimensioning of the deflecting elements used, relative to the observation pupils within the illuminating unit, that as small as possible a vignetting of the observation beam paths takes place due to the deflecting elements, and that a satisfactory image, i.e. in ophthalmic surgery a "red reflection" with high contrast, is also presented to the respective observer with the non-optimal illuminating configuration.

The modular construction of the arrangement according to the invention moreover permits a series of possibilities of variation with regard to the relative arrangement of the individual modules, such as the main observer and co-observer microscopes, the illumination unit, etc.

BRIEF DESCRIPTION OF THE DRAWINGS

Further advantages, and also details of the stereo microscope arrangement according to the invention, will become apparent from the following description of preferred embodiments with reference to the accompanying drawings, in which:

FIGS. 1a and 1b respectively show a plan view of the objective, through which the observation beam paths pass in common, with portions of the illuminating unit in different relative positions;

FIGS. 2a and 2b show another embodiment of the illuminating unit, with deflecting elements arranged differently than those in FIGS. 1a and 1b, in different relative positions;

DETAILED DESCRIPTION OF PREFERRED EMBODIMENTS

Figure 3A:
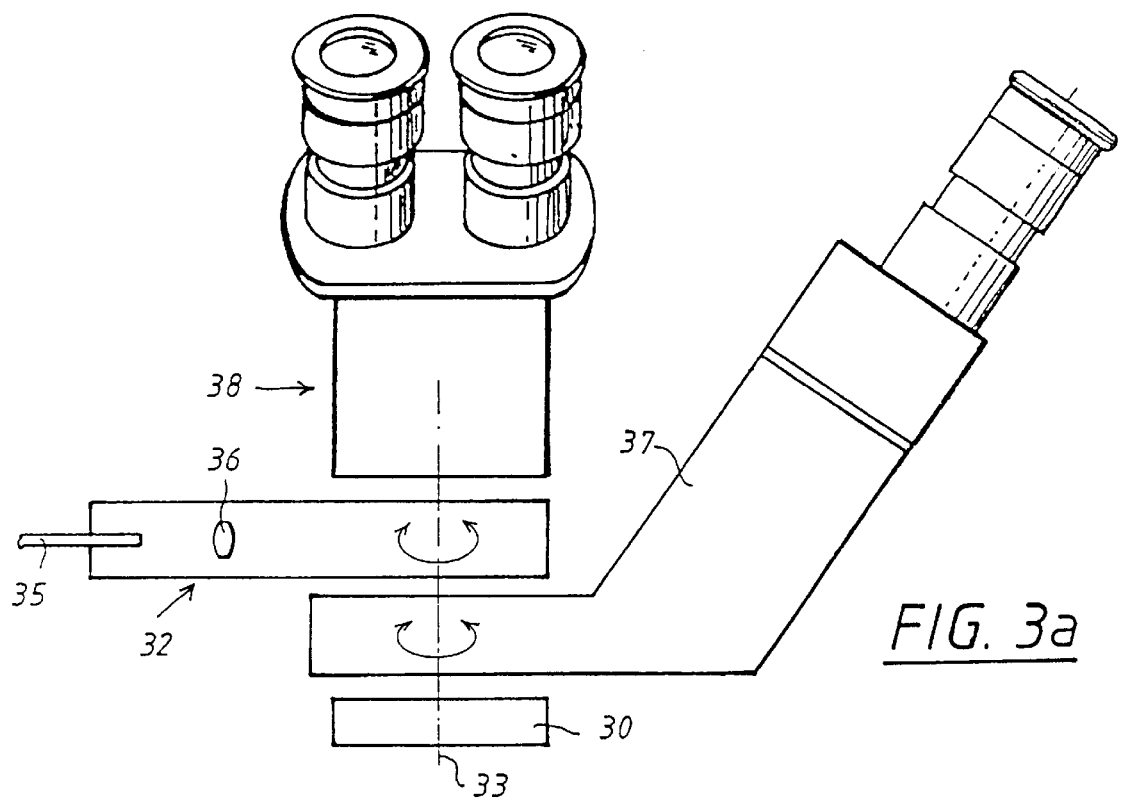
FIGS. 3a and 3b respectively show a side view of different embodiments of the stereo microscope arrangement according to the invention.

A first embodiment of the stereo microscope arrangement according to the invention is shown in FIGS. 1a and 1b. The two Figures respectively show a plan view of the objective (1), through which all the observation beam paths (Ia, Ib, IIa, IIb) pass in common, and also portions of the illuminating unit (2) which is provided. In the two illustrations, the illuminating unit (2) is shown in two different positions relative to the optical axis (3) of the objective (1), or to the stereoscopic observation beam paths (Ia, Ib, IIa, IIb).

The objective (1) which is used in common has, in the embodiment of FIGS. 1a and 1b, two pairs of stereoscopic observation beam paths (Ia, Ib, IIa, IIb) passing through it. Here the larger passage pupils for the stereoscopic observation beam paths (Ia, Ib) are associated with the main observer (I), while the passage pupils, displaced by 90°, of the stereoscopic observation beam paths (IIa, IIb) are available to the co-observer (II) via the co-observer microscope. The orientation for the main observer and for the co-observer is moreover indicated by the two arrows and the associated reference symbols (I, II), where the reference symbol (I) is to represent the main observer orientation, and the reference symbol (II) the co-observer orientation.

Deflecting elements (4a, 4b) in the form of two deflecting mirrors of the illuminating unit (2) can be distinguished, arranged above the objective; they deflect, in the direction of the object plane, respective given portions of the illuminating light incident on them. As regards the arrangement of the deflecting elements (4a, 4b) in the illuminating beam path, reference may be explicitly made here to U.S. Pat. No. 5,126,877,which is incorporated herein by reference. Alternatively, suitable prisms with wavelength-selective coatings, etc., can of course be utilized as the deflecting elements (4a, 4b) within the illuminating device (2) according to the invention.

The illuminating unit (2), which can be mounted in at least two different positions relative to the optical axis (3) of the objective (1), advantageously furthermore includes, in addition to the deflecting elements (4a, 4b), a fiber optic light guide (5) and also an imaging optics (6) arranged in front of the exit surface of the fiber optic light guide. Light from a suitable light source is coupled into the fiber optic light guide (5) on the entry side; this is not illustrated in FIGS. 1a and 1b.

All the elements of the illuminating unit (2) are arranged in a common housing, in the embodiment shown.

A beam dimensioning of the illuminating light takes place in the desired manner by means of the imaging optics (6), which is shown schematically, before the deflection by the deflecting elements (4a, 4b) in the direction of the object plane takes place. Within the illuminating unit (2) according to the invention, alternative arrangements of the imaging optics, the fiber optic light guide, the light source, etc., can be effected throughout.

The relative arrangement of the passage pupils of the stereoscopic observation beams paths (Ia, Ib, IIa, IIb) of the main observer and co-observer, and also the deflecting elements (4a, 4b) or their projection into the objective plane, are now chosen or dimensioned so that, in each of the possible relative positions of the illuminating unit (2), there takes place as small as possible a vignetting of the observation beam paths provided (Ia, Ib, IIa, IIb), or of their associated passage pupils.

In FIG. 1a, the illuminating unit (2) is arranged immediately opposite the main observer (I), and in this position places the optimum illuminating configuration at the disposal of the main observer (I). The two deflecting elements (4a, 4b) are arranged, in this embodiment, at angles of about 2° and about 6° relative to the optical axis (3); in principle, alternative relative angles can always be realized.

According to the invention, the illuminating unit (2), respectively the corresponding deflecting elements (4a, 4b) can be arranged in at least one further alternative position relative to the observation beam paths (Ia, Ib, IIa, IIb). The deflecting elements (4a, 4b) assume the same angle to the optical axis (3) in this at least one alternative position. This position is shown in FIG. 1b, where the illuminating unit (2) is now arranged opposite the co-observer (II) and in this manner the co-observer has the optimized illuminating configuration, with the deflecting elements (4a, 4b) in the optimum angular positions, at his disposal. Even in the case of the position of the illuminating unit (2) according to FIG. 1b, it is ensured that an acceptable illuminating configuration and a corresponding image quality are available for the main observer (I). For this purpose, the deflecting elements (4a, 4b) are geometrically dimensioned, and arranged relative to the observation beam paths (Ia, Ib, IIa, IIb), such that the smallest possible vignetting of the observation beam paths results in all possible positions of the illuminating unit.

The illuminating unit (2) can be arranged, according to the invention, in either of only two different discrete positions relative to the stereoscopic observation beam paths (Ia, Ib, IIa, IIb). However, it is also possible to arrange the illuminating unit (2), for example, to be continuously rotatable about the optical axis (3) of the objective (1), so that many intermediate positions are available.

It is furthermore not necessary for the different possible positions of the illuminating unit to be arranged with rotational symmetry about the optical axis of the objective; i.e., the illuminating unit can also be arranged to be displaced about an axis which does not correspond to the optical axis of the objective, and so on.

With a rotation of the illuminating unit (2), the objective (1) which is used in common can selectively either remain fixed in its position or else be correspondingly displaced with the rotary motion of the illuminating unit (2).

Moreover it is also found to be advantageous to design the relative orientation of the observation beam paths (Ia, Ib, IIa, IIb) of the main observer and the co-observer to be variable relative to each other. This can take place, for example, by means of a main observer microscope and co-observer microscope which are correspondingly rotatable about a common axis.

A further embodiment of the illuminating unit (12) arranged according to the invention is shown in FIGS. 2a and 2b. The illuminating unit (12) again assumes two different positions relative to a defined axis.

However, one difference from the first embodiment of FIGS. 1a and 1b is that here another arrangement of the deflecting elements (14a, 14b) within the illuminating unit (12) according to the invention is provided. Thus one of the two deflecting elements (14a, 14b) is respectively arranged on the opposite side of the stereoscopic observation beam paths (Ia, Ib, IIa, IIb).

This further embodiment gives expression to the fact that it is not the special arrangement of the deflecting elements (14a, 14b) within the illuminating unit (2) which is inventively important, but the optional placing of the optimum illuminating configuration for the stereoscopic observation beam paths (Ia, Ib, IIa, IIb) at the disposal of the main observer (I) or the co-observer (II).

Again, in FIG. 2a the position of the illuminating unit (2) or of the deflecting elements (4a, 4b) is first shown in an optimized relative position for the main observer (I). Again, in the projection of the deflecting element surfaces in the objective plane, there takes place only a small vignetting of the observation pupils. The rotated illuminating unit (12) is shown in FIG. 2b, and is arranged at a displacement of 90° relative to FIG. 1a; the optimum illuminating conditions are now at the disposal of the co-observer.

Both in the embodiment of FIGS. 1a and 1b and also in the embodiment of FIGS. 2a and 2b, there is respectively provided an arrangement of the main observer and co-observer microscopes which is displaced by 90°; however, this is not of inventive importance.

In the embodiment of FIGS. 2a and 2b, the illuminating unit (12) is arranged to be rotatable about an axis of symmetry which is displaced from the optical axis of the objective. Also, the four illustrated passage pupils of the stereoscopic observation beam paths (Ia, Ib, IIa, IIb) are arranged in relation to the objective (10) to be non-centered with respect to the optical axis of the objective. Again, what is important is only that the illuminating unit (12) can be arranged or mounted in at least two different positions relative to the stereoscopic observation beam paths (Ia, Ib, IIa, IIb). Consequently the rotation is possible about an axis of symmetry which is surrounded by the four observation beam paths (Ia, Ib, IIa, IIb) provided.

Figure 3B:
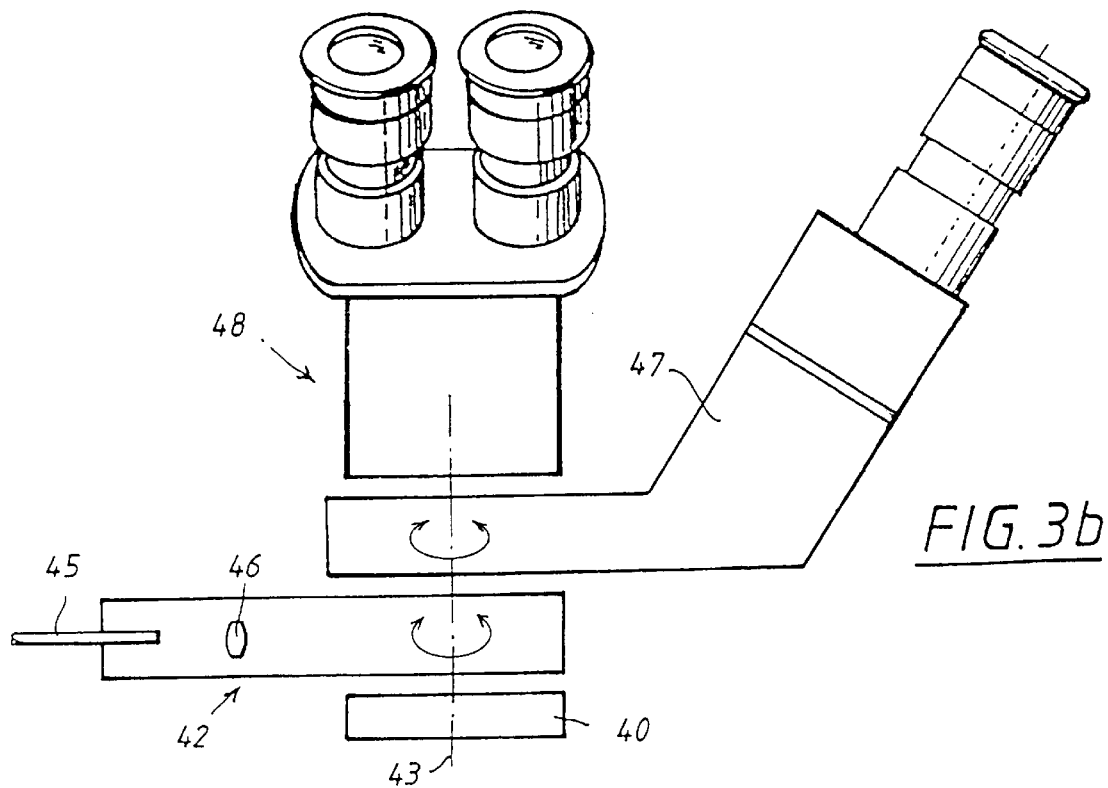

Side views of respective different embodiments of the stereo microscope arrangement according to the invention are shown schematically in FIGS. 3a and 3b.

In FIG. 3a, a co-observer microscope (37) is arranged over the objective (30) through which all the observation beam paths pass in common, and is rotatable about the optical axis (33) of the objective (30). The illumination unit (32), arranged above the co-observer microscope (37) and according to the invention likewise rotatable about this axis (33), is shown in an optimum position for the co-observer.

It is advantageous here to make the optimum positions of the illumination unit (32), which respectively correspond to an arrangement displaced by 180° with respect to the respective observer, easily recognizable by the observer, e.g. by means of a latching mechanism. Thus the observer can quickly, and without great adjustment effort, find the position of the illuminating unit (32) which is optimum for him, for example during an operation.

Above the illuminating unit (32) with a fiber optic light guide (35), imaging optics (36) and the deflecting elements (not shown), there again follows, in a known manner, the main observer microscope (38), with a pancratic magnification system, binocular tube, etc.

Alternatively to this, it is also possible, according to the embodiment of FIG. 3b, to interchange along the optical axis (43) the arrangement of the illuminating unit (42) and the co-observer microscope (47), and now to provide the illuminating unit (42), which can be mounted in at which can be mounted in at least two different relative positions to the observation beam paths, directly above the objective (40), which is used in common. Above the illuminating unit (42), which can be mounted in different positions, the interface is provided for the rotatably arranged co-observer microscope (47). The illuminating unit according to the invention again includes a fiber optic light guide (35), an imaging optics (36), and the deflecting elements (not shown), as previously described.

Besides the possibility of continuous rotatability of the co-observer microscope, it is furthermore possible to provide the co-observer microscope as mountable only in discrete positions relative to the main observer microscope. This can for example be effected by means of a corresponding plug-in connection for the co-observer microscope, etc.

In a further embodiment there can be provided for defined variability of the stereo base. This variability of the stereo base is provided for in particular in the co-observer microscope. This can take place, for example, by means of a pair of planar plates, prisms, or the like, which are movably arranged in the observation beam paths. A suitable arrangement of this kind is described in German Patent DE 44 07 590, which corresponds to U.S. patent application Ser. No. 223,333, filed Apr. 5, 1994 U.S. Pat. No. 5,537,248.

It is thereby ensured that a stereo base can always be adjusted to correspond to the respective conditions.

I claim:

1. Stereo microscope arrangement comprising:
   at least a first and a second pair of stereoscopic observation beam paths,
   an objective used in common by said at least first and second pair of stereoscopic observation beam paths, and
   an illuminating unit with at least one deflecting element that deflects illuminating light in a direction of an object plane,
   wherein relative to said object plane said at least one deflecting element is on the same side as said objective for observing said object plane in reflected light, and
   wherein said illuminating unit including said at least one deflecting element moveably mounted in at least two different positions in a plane substantially orthogonal to said at least first and second pair of stereoscopic observation beam paths, and said at least one deflecting element deflects illuminating light in a direction of said object plane in both of said at least two different positions.

2. Stereo microscope arrangement according to claim 1, wherein said illuminating unit is arranged to be continuously rotatable about said optical axis of said objective.

3. Stereo microscope arrangement according to claim 1, wherein said illuminating unit includes two deflecting elements that deflect light at different angles relative to an optical axis of said objective in a direction of an object plane.

4. Stereo microscope arrangement according to claim 3, wherein said two deflecting elements are arranged at angles of 2° and 6° respectively relative to said optical axis of said objective.

5. Stereo microscope arrangement according to claim 1, wherein said first pair of stereoscopic observation beam paths is embodied as main observer beam paths in a main observer microscope, and said second pair of stereoscopic observation beam paths is embodied as co-observer beam paths in a co-observer microscope.

6. Stereo microscope arrangement according to claim 5, wherein said main observer microscope and said co-observer microscope are arranged to be rotatable relative to each other about an optical axis of said objective.

7. Stereo microscope arrangement according to claim 1, wherein said illuminating unit includes a plurality of deflecting elements arranged such that projection of said deflecting elements in a plane of said objective causes as small as possible a vignetting of observation pupils passing through said objective.

8. Stereo microscope arrangement according to claim 1, wherein said illuminating unit includes a fiber optic light guide with an exit surface and at least one imaging optics for beam dimensioning arranged between said exit surface of said fiber optic light guide and said at least one deflecting element.

9. An illuminating unit for a stereo microscope,
   said stereo microscope comprising:
      a main-observer microscope optically and mechanically coupled to at least one co-observer microscope, and
      an objective through which all stereoscopic observation beam paths of said stereo microscope pass in common,
      said illuminating unit comprising at least one deflecting element that deflects illuminating light in a direction of an object plane,
      wherein said at least one deflecting element and said objective are on the same side relative to said object plane for observing said object plane in reflected light, and
      wherein said illuminating unit including said at least one deflecting element moveably mounted in at least two different positions in a plane substantially orthogonal to said stereoscopic observation beam paths, and said at least one deflecting element deflects illuminating light in a direction of said object plane in both of said at least two different positions.

10. Illuminating unit according to claim 9, further comprising a fiber optic light guide having an exit surface, an imaging optics arranged in front of said exit surface, and a common housing in which all elements of said illuminating unit are arranged.

11. Stereo microscope arrangement comprising:
    at least a first and a second pair of stereoscopic observation beam paths,
    an objective used in common by said at least first and second pair of stereoscopic observation beam paths, and an illuminating unit with at least one deflecting element that deflects illuminating light in a direction of an object plane, wherein relative to said object plane said at least one deflecting element is on the same side as said objective for observing said object plane in reflected light, wherein said illuminating unit including said at least one deflecting element moveably mounted in at least two different positions in a plane substantially orthogonal to said at least first and second pair of stereoscopic observation beam paths, and said at least one deflecting element deflects illuminating light in a direction of said object plane in both of said at least two different positions, and wherein said objective is together with said illuminating unit mountable in at least two different positions around an optical axis of said objective.

12. Stereo microscope arrangement comprising:

at least a first and second pair of stereoscopic observation beam paths, an objective used in common by said at least first and second pair of stereoscopic observation beam paths, and an illuminating unit with at least one deflecting element that deflects illuminating light in a direction of an object plane, wherein relative to said object plane said at least one deflecting element is on the same side as said objective for observing said object plane in reflected light, wherein said illuminating unit including said at least one deflecting element moveably mountable in at least two different positions in a plane substantially orthogonal to said at least first and second pair of stereoscopic observation beam paths, and said at least one deflecting element deflects illuminating light in a direction of said object plane in both of said at least two different positions, and wherein said objective is together with said illuminating unit rotatable into at least two different positions around an optical axis of said objective.

* * * * *